(12) United States Patent
Teplitzky

(10) Patent No.: US 11,763,943 B2
(45) Date of Patent: Sep. 19, 2023

(54) AUTOMATED VENTRICULAR ECTOPIC BEAT CLASSIFICATION

(71) Applicant: Preventice Solutions, Inc., Rochester, MN (US)

(72) Inventor: Benjamin A. Teplitzky, Minneapolis, MN (US)

(73) Assignee: Preventice Solutions, Inc., Rochester, MN (US)

( * ) Notice: Subject to any disclaimer, the term of this patent is extended or adjusted under 35 U.S.C. 154(b) by 0 days.

(21) Appl. No.: 16/283,159

(22) Filed: Feb. 22, 2019

(65) Prior Publication Data

US 2019/0272920 A1 Sep. 5, 2019

Related U.S. Application Data

(60) Provisional application No. 62/637,738, filed on Mar. 2, 2018.

(51) Int. Cl.
*G16H 50/20* (2018.01)
*G06N 3/08* (2023.01)
(Continued)

(52) U.S. Cl.
CPC .............. *G16H 50/20* (2018.01); *G06N 3/045* (2023.01); *G06N 3/08* (2013.01); *G16H 40/63* (2018.01)

(58) Field of Classification Search
CPC .......... G16H 50/20; G06N 20/00; G06N 3/08; G06N 5/02; G06N 5/04; G06N 20/10; G06N 3/006; G06N 3/04; G06N 3/0454; G06N 3/049; G06N 3/061; G06N 7/005; G06N 3/0445; G06N 3/084; G06N 3/0472; G06N 5/003; G06N 20/20; G06N 3/00; G06N 3/02; G06N 3/0481; G06N 3/063;
(Continued)

(56) References Cited

U.S. PATENT DOCUMENTS 9,161,705 B2   10/2015 Tamil et al.
10,426,364 B2  10/2019 Rapin et al.
(Continued)

OTHER PUBLICATIONS

Yelei Li, Heartbeat Detection, Classification And Coupling Analysis Using Electrocardiography Data, Aug. 2014, Case Western Reserve University (Year: 2014).*
(Continued)

*Primary Examiner* — Ann J Lo
*Assistant Examiner* — Charles C Kuo
(74) *Attorney, Agent, or Firm* — Faegre Drinker Biddle & Reath LLP

(57) ABSTRACT

Techniques for classifying heartbeats using patient electrocardiogram (ECG) data are described. ECG data is received, including waveform data and time interval data relating to a plurality of heartbeats for the patient. A convolutional neural network in a first path of a machine learning architecture generates a first plurality of output values by analyzing the waveform data. A fully-connected neural network in a second path of the machine learning architecture generates a second plurality of output values by analyzing the time interval data. The plurality of heartbeats in the ECG data are classified by concatenating the first plurality of output values and the second plurality of output values using the machine learning architecture.

20 Claims, 6 Drawing Sheets

(51) Int. Cl.
*G16H 40/63* (2018.01)
*G06N 3/045* (2023.01)

(58) Field of Classification Search
CPC ........ G06N 3/082; G06N 3/086; G06N 3/088; G06N 3/126
See application file for complete search history.

(56) References Cited

U.S. PATENT DOCUMENTS

| | | | |
|---|---|---|---|
| 10,758,139 | B2 | 9/2020 | Rapin et al. |
| 10,779,744 | B2 | 9/2020 | Rapin et al. |
| 2016/0292373 | A1* | 10/2016 | Spors ..................... G16H 40/63 |
| 2017/0112401 | A1 | 4/2017 | Rapin et al. |
| 2019/0059763 | A1* | 2/2019 | Shakur ............... A61B 5/04012 |

OTHER PUBLICATIONS

Pranav Rajpurkar et al., Cardiologist-Level Arrhythmia Detection with Convolutional Neural Networks, Jul. 2017 (Year: 2017).*

Shiqing Zhang et al., Multimodal Deep Convolutional Neural Network, Jun. 2016, ICMR '16, pp. 281-284 (Year: 2016).*

J. P. Kelwade, Prediction of Cardiac Arrhythmia using Artificial Neural Network , Apr. 2015, International Journal of Computer Applications (0975-8887) vol. 115—No. 20, Apr. 2015, pp. 30-35 (Year: 2015).*

Moacir P. Ponti Jr., Combining Classifiers: From the Creation of Ensembles to the Decision Fusion (2011), IEEE 24th SIBGRAPI Conference on Graphics, Patterns, and Images Tutorials (Year: 2011).*

Ming Li et al., Verification Based ECG Biometrics with Cardiac Irregular Conditions Using Heartbeat Level and Segment Level Information Fusion, 2014 IEEE International Conference on Acoustic, Speech and Signal Processing (ICASSP), pp. 3769-3773 (Year: 2014).*

Lin et al., Heartbeat Classification Using Normalized RR Intervals and Morphological Features, 2014 (Year: 2014).*

Tae Joon Jun et al. "Premature ventricular contraction beat detection with deep neural networks," 2016 15th IEEE International Conference on Machine Learning and Applications, 6 pages.

* cited by examiner

AUTOMATED VENTRICULAR ECTOPIC BEAT CLASSIFICATION

CROSS-REFERENCE TO RELATED APPLICATIONS

This application claims benefit to U.S. provisional application Ser. No. 62/637,738 filed on Mar. 2, 2018. The aforementioned related patent application is herein incorporated by reference in its entirety.

BACKGROUND

Portable monitoring devices for collecting biometric data are becoming increasingly common in diagnosing and treating medical conditions in patients. Mobile cardiac telemetry (MCT), which can be used to record electrocardiogram (ECG) data for patients, is one example of this. MCT empowers physicians with valuable information regarding the occurrence and regularity of a variety of heart conditions and irregularities. As one example, Ventricular Ectopic Beats (VEB) are a sub-category of abnormal heart contractions, which originate from the ventricles. For some patients, these beats signify a potentially life-threatening and treatable cardiac irregularity. MCT can be used to monitor VEBs using ECG data, among other conditions.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DESCRIPTION OF EXAMPLE EMBODIMENTS

Overview

Figure 1:
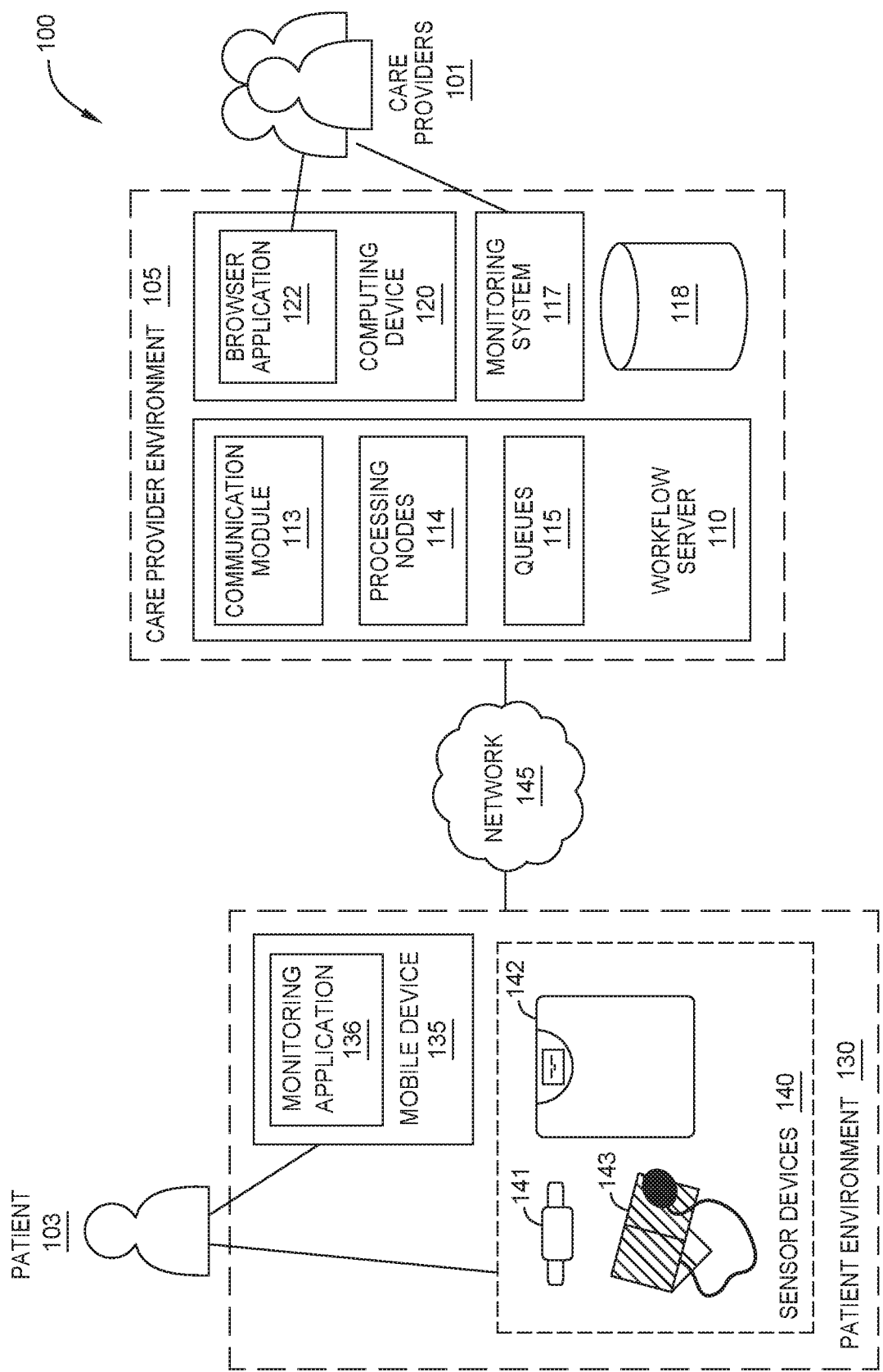
FIG. 1 illustrates an example computing environment, according to one embodiment described herein.

One embodiment provides a computer-implemented method for classifying heartbeats using patient electrocardiogram (ECG) data. The method includes receiving the ECG data for the patient. The ECG data includes waveform data and time interval data relating to a plurality of heartbeats for the patient. The method further includes generating a first plurality of output values by analyzing the waveform data using a convolutional neural network in a first path of a machine learning architecture. The method further includes generating a second plurality of output values by analyzing the time interval data using a fully-connected neural network in a second path of the machine learning architecture. The method further includes classifying one or more of the plurality of heartbeats in the ECG data by concatenating the first plurality of output values and the second plurality of output values using the machine learning architecture.

Another embodiment provides a computer program product for classifying heartbeats using patient ECG data. The computer program product includes a computer-readable storage medium having computer-readable program code embodied therewith, the computer-readable program code executable by one or more computer processors to perform an operation. The operation includes receiving the ECG data for the patient. The ECG data includes waveform data and time interval data relating to a plurality of heartbeats for the patient. The operation further includes generating a first plurality of output values by analyzing the waveform data using a convolutional neural network in a first path of a machine learning architecture. The operation further includes generating a second plurality of output values by analyzing the time interval data using a fully-connected neural network in a second path of the machine learning architecture. The operation further includes classifying one or more of the plurality of heartbeats in the ECG data by concatenating the first plurality of output values and the second plurality of output values using the machine learning architecture.

Another embodiment provides a system. The system includes a processor and a memory storing a program, which, when executed on the processor, performs an operation. The operation includes receiving ECG data for a patient. The ECG data includes waveform data and time interval data relating to a plurality of heartbeats for the patient. The operation further includes generating a first plurality of output values by analyzing the waveform data using a convolutional neural network in a first path of a machine learning architecture. The operation further includes generating a second plurality of output values by analyzing the time interval data using a fully-connected neural network in a second path of the machine learning architecture. The operation further includes classifying one or more of the plurality of heartbeats in the ECG data by concatenating the first plurality of output values and the second plurality of output values using the machine learning architecture.

Example Embodiments

Interpreting and summarizing ECG data and MCT study results is a time-consuming process. MCT is commonly prescribed for 10 to 30 days, generating large amounts of ECG data. Generally, ECG data includes waveforms identifying electrical activity relating to patient heart activity. ECG data is captured by service providers, annotated, and summarized into patient-specific reports for clinicians. The growing popularity of MCT results in a need for high-performance algorithms to analyze and classify the collected data.

In an embodiment, machine learning can be used to classify data collected using MCT (e.g., ECG data). For example, deep learning and neural network architectures can be used to produce a classification model for ECG data collected using MCT. In one example, a machine learning model can classify heartbeats (e.g., as VEBs) in ECG data collected using MCT. The model can provide a high degree of sensitivity and specificity in classifying heartbeats, without requiring time-consuming patient-specific labeling of training data.

In an embodiment, the classification model can be trained using ECG data collected from real patients using an MCT device. This data can also be collected using a holter monitor or any other suitable device that provides ECG data. The trained model can then be deployed as part of a care provider environment, and can be used to classify VEBs and other cardiac events. The output from the model can be used to improve patient care. For example, the output can be provided to physicians or patients to facilitate diagnosis and treatment of cardiac irregularities. The output can also be stored in an electronic data repository, and used to generate reports or patient care plans.

In an embodiment, as discussed further below with regard to FIGS. 4-6, a machine learning architecture incorporating two paths can be used. A deep convolutional network can operate on heartbeat waveform data. A fully-connected neural network can operate on heart rate time-interval data. The output from the deep convolutional network can be combined with the output from the fully-connected neural network. This architecture can result in improved accuracy and performance for the model. This is discussed further in the paper Fully-Automated Ventricular Ectopic Beat Classification for Use with Mobile Cardiac Telemetry, provided as Appendix A with U.S. provisional application No. 62/637,738. As noted above, this provisional application, including Appendix A and the other appendices, is herein incorporated by reference.

Patient Care Environment

FIG. 1 illustrates an example computing environment 100, according to one embodiment described herein. As shown, the computing environment 100 may include a care provider environment 105 and a patient environment 130, each connected to one another via a network 145. The care provider environment 105 and the patient environment 130 allow a care provider 101 (e.g., a technician, nurse, physician, etc.) to monitor biometric data generated by the patient 103.

The care provider environment 105 includes a workflow server 110, a computing device 120, monitoring system 117 and data repository 118. Each of the workflow server 110, the computing device 120, and the monitoring system 117 may be a physical computing system or a virtual computer instance (e.g., executing in a cloud computing platform). A care provider 101 may use the computing device 120 to access (e.g., via a browser application 122, a native application on device 120, etc.) a user interface (UI) hosted by the monitoring system 117.

Of note, although shown as a single entity, the data repository 118 can represent multiple, separate data stores (e.g., relational databases). Moreover, these data stores can span multiple computing nodes. To this end, the separate data stores could be made to function as a single data store (e.g., through data replication techniques and through the use of load balancers). As such, the data repository 118 is representative of any sort of data store on any number of computing systems, consistent with the functionality described herein.

Additionally, although not shown, the data repository 118 may store data from and/or service requests from various other entities, such as third party applications, partners and affiliates, electronic medical record systems, external monitoring devices and products, analytics engines, data consolidator applications and so on. More generally, it is contemplated that the data repository 118 and, more generally, other elements within the care provider environment 105, can interact with any number of different data originators and receipts, consistent with the functionality described herein. As such, the computing environment 100 is provided merely for illustrative purposes only and without limitation.

The workflow server 110 includes applications and data executed to identify and handle health events corresponding to the patient 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and the queues 115 which form a workflow. As the biometric data or health events are received from the patient environment 130, the workflow may classify (or reclassify) the data to identify a type of the health event—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicated an electrode has become detached triggers a maintenance event. In one embodiment, at least one sensor device 140 within the patient environment 130 or a monitoring application 136 installed as part of a mobile device 135 within the patient environment 130 may have performed an initial classification of the data or health events. Nonetheless, the workflow server 110 may evaluate the biometric data (or maintenance data) to confirm that this initial classification was correct.

Each type of health event may take a different path through the workflow. That is, different health events may traverse the processing nodes 114 and the queues 115 using different paths. For example, a cardiac event may be evaluated using different processing nodes 114 in the server 110 than a maintenance event. Furthermore, paths through the workflow for the same health event may differ based on a variety of factors such as the severity of the health event, age of the patient 103, other symptoms exhibited by the patient 103, medication taken by the patient 103, and the like. For example, a high priority cardiac event may skip one or more of the processing nodes 114 or the queues 115 and be immediately displayed to the care provider 101 using the monitoring system 117.

The communication module 113 permits the workflow server 110 to receive the data from the patient environment 130 and transmit data to the care providers 101. The communication module 113 may receive data from the at least one sensor device 140 which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the workflow server 110 to transmit requests or instructions to the patient environment 130 such as asking the patient 103 if she has any symptoms or instructing the patient 103 to reattach a disconnected electrode (not shown) of the at least one sensor device 140.

In one embodiment, a path used by a health event to traverse the workflow server 110 may include processing nodes 114 that process the health event without user intervention as well as the processing nodes 114 that require input from the care providers 101. For example, one of the processing nodes 114 may filter or screen a health event to determine what queue to place the event, compare the event to one or more rules to determine an action to perform, or store the event. Alternatively, others of the processing nodes 114 may require the care provider 101 to perform an action or provide instructions. For example, the monitoring system 117 may generate a user interface (UI) for a health event which is then displayed to the care provider 101 by the browser application 122. Once the care provider 101 performs an action (e.g., confirms the classification of the event or agrees with an action suggested by the workflow server 110), the remaining operations of the workflow are performed—e.g., send a notification to the patient 103, log the event in the history of the patient 103, route the event to a different one of the care providers 101, reclassify the health event (if the care provider 101 indicated the initial classification was incorrect), or prioritize or triage the health event.

With continued reference to FIG. 1, the patient environment 130 includes the mobile device 135 and the at least one sensor device 140. The mobile device 135 includes the monitoring application 136 which permits communication between the at least one sensor device 140 and the care provider environment 105 via the network 145. The monitoring application 136 may configure the at least one sensor device 140 (e.g., IoT devices) to monitor biometric data of the one or more patient 103 as specified by a care plan. For example, the monitoring application 136 could configure logic on a heart rate monitoring device worn by the patient to monitor the patient's heart rate. In turn, the monitoring application 136 can send the heart rate data to the workflow server 110 which determines if a heath event is triggered, and if so, executes a workflow to process the event as described above. In another embodiment, the heart rate monitoring device, upon detecting that a threshold condition has been satisfied, could generate and transmit a health event to the mobile device 135, which in turn transmits the health event to the workflow server 110 for processing. However, in other embodiments, some of the tasks performed by the workflow server 110 may be performed by the mobile device 135. That is, the workflow may include tasks performed by the mobile device 135 or the at least one sensor device 140 as well as tasks performed by the workflow server 110.

In one embodiment, the monitoring application 136 receives environmental data from the at least one sensor device 140. Generally, the environmental data informs the monitoring application 136 of environmental conditions in an area proximate to the at least one sensor device 140 and the user—e.g., a room in which the user is located. For example, the at least one sensor device 140 may detect an air quality or pollen count for the patient 103 having a respiratory ailment. In another example, the at least one sensor device 140 may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the mobile device 135 which permits the patient 103 to list symptoms. Moreover, the monitoring application 136 may also display general information related to a care plan or the at least one sensor device 140 such as the patient's heart rate or weight, status of the at least one sensor device 140, etc.

In one embodiment, the at least one sensor device 140 interacts with the monitoring application 136 and assists the patient 103 in reporting patient vitals and other information to the care provider environment 105. As shown, the at least one sensor device 140 may include a body sensor 141, a weighing scale 142, and a blood pressure cuff 143. Each of the at least one sensor device 140 may capture different vitals of the patient 103. For example, when applied to a body of patient 103, the body sensor 141 captures biometric data (e.g., heart rate, ECG data, etc.) in real-time. In addition, each of the at least one sensor device 140 may be configured to transmit body-related metrics electronically to the monitoring application 136 on the mobile device 135. In turn, the monitoring application 136 sends the captured metrics to the workflow server 110 which can be used to trigger health events which are processed using the processing nodes 114 and the queues 115.

In one embodiment, upon detecting an observation threshold has been reached, the at least one sensor device 140 performs an initial classification of the health event. In a particular embodiment, the mobile device 135 is configured to perform the initial classification of the health event. For example, the body sensor 141, upon detecting that ECG data collected from the patient 103 indicates an erratic heart behavior, could classify the health event as a cardiac event. This initial classification of the health event, along with the relevant ECG data (e.g., ECG data including a predetermined length of time before and after the event), could be transmitted to the mobile device 135 (e.g., over a Bluetooth® communications link) and the monitoring application 136 subsequently forwards the ECG data and the health event data on to the workflow server 110 over the network 145 (e.g., the Internet). Alternatively, instead of classifying the data, the monitoring application 136 may forward the raw, unprocessed sensor data to the workflow server 110 which uses one of the processing nodes 114 to identify and classify health events which are then processed in the workflow server 110.

Figure 2:
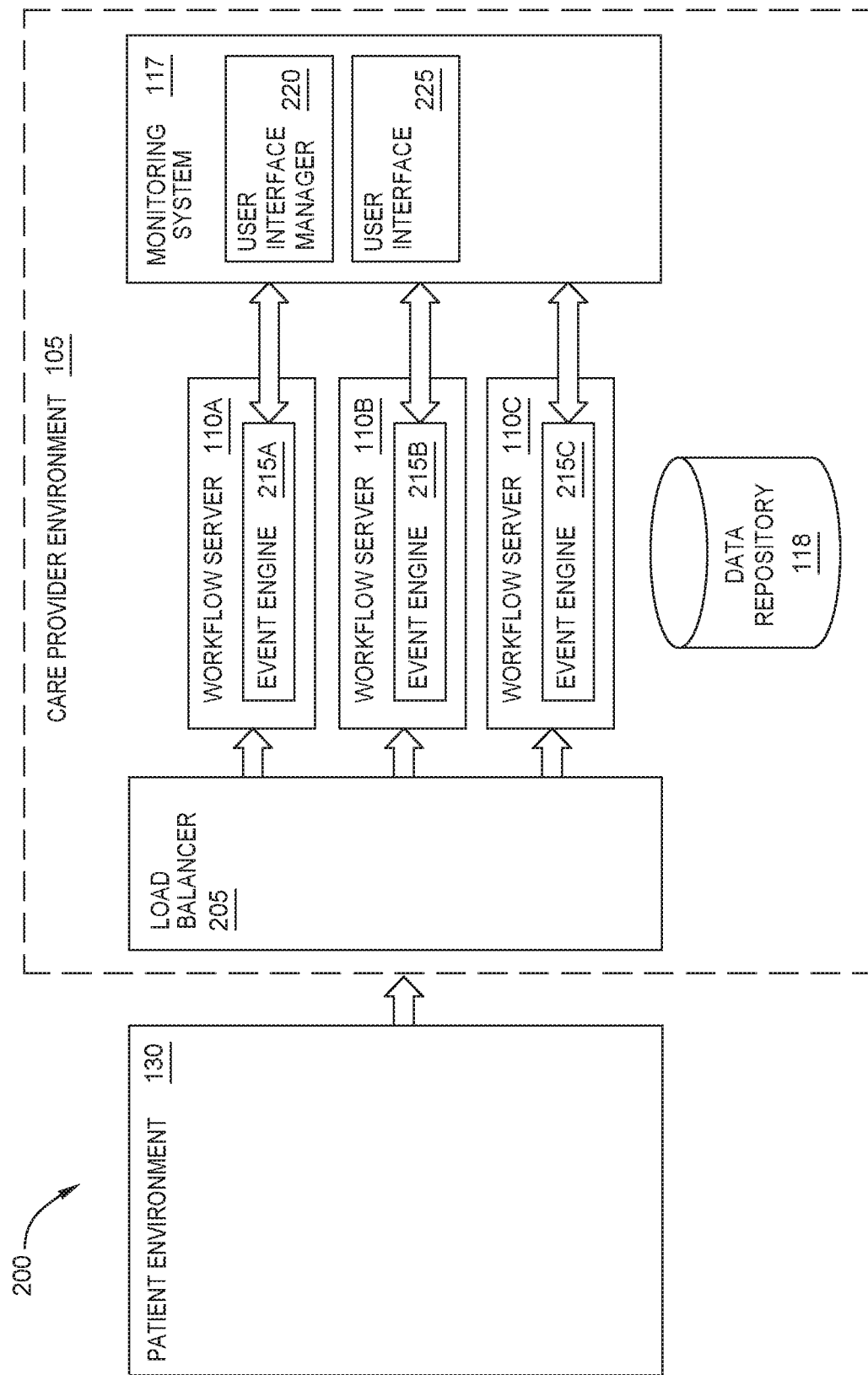
FIG. 2 illustrates a parallel processing computing environment, according to one embodiment described herein.

FIG. 2 illustrates a parallel processing computing environment 200, according to one embodiment described herein. As shown, the patient environment 130 transmits biometric data and/or health events to the care provider environment 105 which includes a load balancer 205. The workflow servers 110A-110C each include a respective one of the event engines 215A-215C. Although not shown, each of the event engines 215A-215C includes a plurality of interconnected processing nodes and queues that form a workflow for processing health events as discussed above. In one embodiment, the event engines 215A-215C each includes the same processing nodes and queues arranged in the same manner such that any one of the event engines 215A-215C can process the different health events generated by the at least one sensor device 140—i.e., any one of the event engines 215A-215C can process a cardiac event, respiratory event, maintenance event, etc. Based on current workload, the load balancer 205 transmits received data or heath events to one of the workflow servers 110A-110C for processing. For example, the load balancer 205 may assign the received health events in a round robin manner or by monitoring each respective central processing unit (CPU) or memory usage of the workflow servers 110A-110C.

Alternatively, the event engines 215A-215C may have different processing nodes and queues (or a different arrangement of the nodes and queues) such that the event engines 215A-215C are configured to process different event types. For example, the event engines 215A, 215B may have workflows that process cardiac events (and have the same processing nodes and queues), while the workflow in the event engine 215C processes respiratory events. The load balancer 205 may determine which of the event engines 215A-215C should receive the health event using the initial classification provided by the patient environment 130 or based on which of the at least one sensor device 140 measured the biometric data.

Regardless whether the event engines 215A-215C have the same arrangement or different arrangements, compute resources can easily be adjusted in response to varying workloads. For example, if additional sensor devices (e.g., sensor devices 140) are added to the patient environment 130, a system administrator can add additional ones of the workflow servers 110A-110C to process an increased number of received health events. The reverse is also true. If the number of health events decreases, the administrator may remove one or more of the workflow servers 110A-110C. For example, if the event engines 215A, 215B both process cardiac events but the number of cardiac events has decreased, the system administrator may remove one of the workflow servers 110A, 110B. As another example, a load balancer component could monitor the usage of computational resources by the workflow servers 110A-110C and could scale the number of servers up or down, based on the computational resource usage.

With continued reference to FIG. 2, the monitoring system 117 includes a user interface manager 220 (UI manager) and a user interface 225 (UI). As discussed above, the processing nodes 114 may require input from the care provider 101 (FIG. 1) in order to route the health events through the event engines 215A-215C. To do so, the event engines 215A-215C transmit requests to the UI manager 220 which generates the UI 225 which can be displayed to the care provider 101. For example, the UI manager 220 may generate the UI 225 that includes an electrocardiogram (ECG) chart corresponding to a cardiac event. Further, the UI 225 may include I/O features (e.g., buttons or pull down menus) that the care provider can use to provide input or instructions to one of the event engines 215A-215C. For example, the care provider may instruct the one of the event engines 215A-215C to store the cardiac event in the data repository 118, send the cardiac event to one of the queues 115 (FIG. 1) that is monitored by another care provider (e.g., to get a second opinion), or forward the cardiac event to the care provider 101 of the patient 103. Thus, the monitoring system 117 permits the workflow servers 110 to output information to the care provider 101 as well as receive instructions from the care provider 101.

The event engines 215A-215C may store data in and retrieve data from the data repository 118. For example, the event engines 215 may maintain a patient history by storing all the received health events (or selected health events) derived based on monitoring a patient's vitals in the repository 118. Further, the event engines 215A-215C may use the data stored in the data repository 118 to process the health events. For example, if one of the event engines 215A-215C receives biometric data indicating the current weight of the patient 103, then the one of the event engines 215A-215C can retrieve past weight measurements for the patient 103 from the data repository 118 and derive a trend graph detailing how the weight of the patient 103 has changed over time. For instance, the patient's current weight may not be enough to trigger a health event, but the patient's derived weight change over a period of time may trigger a health event. As discussed below, these derived trends may be used to generate a derived observation (or other event(s)).

In one embodiment, the event engines 215A-215C prioritize health events, which, in turn, determines how quickly the health events are processed by the workflows in the event engines 215A-215C or what processing nodes and queues are used to process the health events. As discussed above, the health events may be prioritized based on a severity of the health event, the type of the health event, a characteristic of the patient 103 whose biometric data generated the health event, and the like. Additionally, the health events could be prioritized based on additional criteria, such as an institutional policy, a care plan-level policy, a patient-level policy, another policy or some combination of the above.

Figure 3:
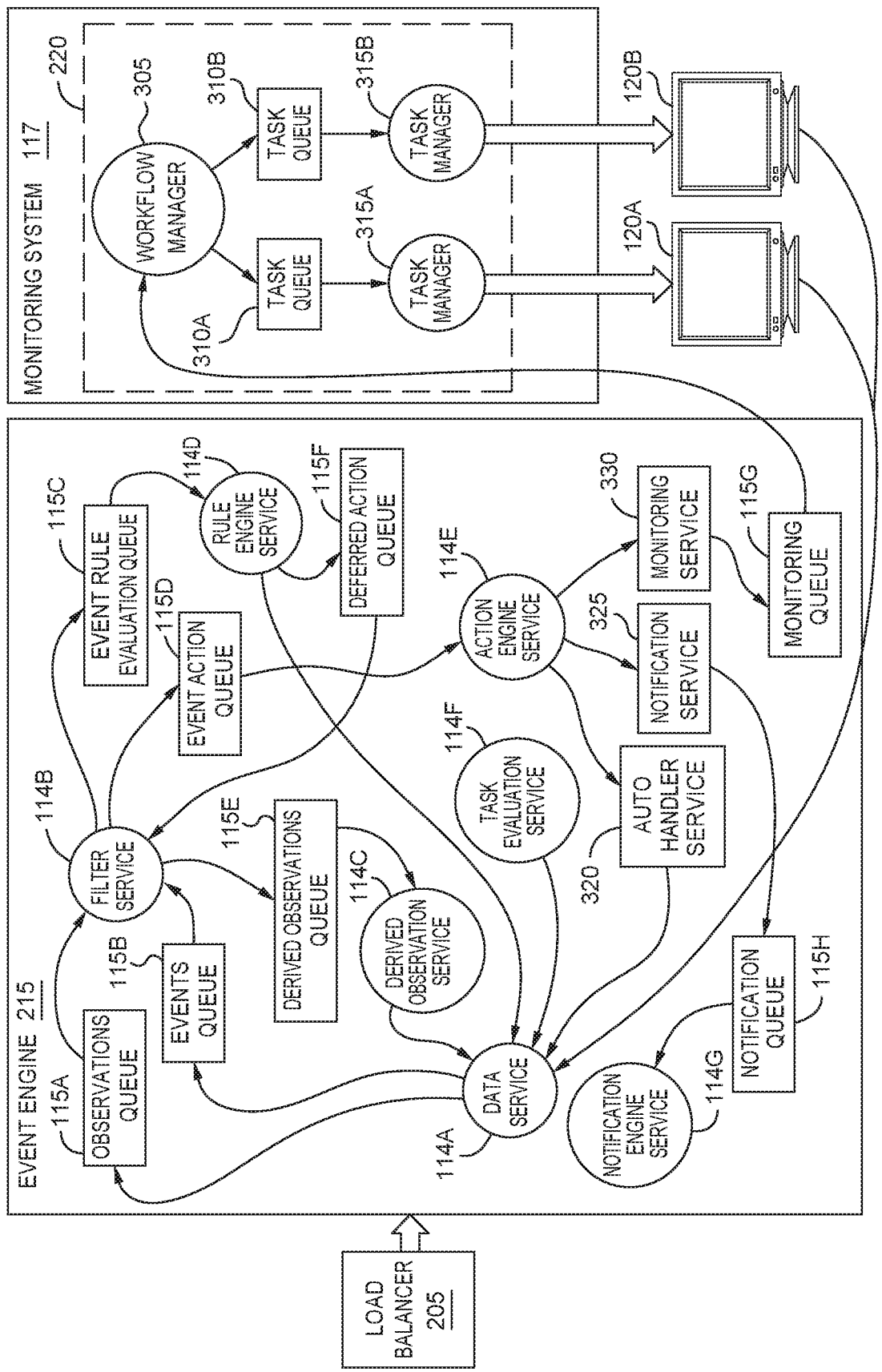
FIG. 3 illustrates an event engine that includes a workflow for processing health events, according to one embodiment described herein.

FIG. 3 illustrates an event engine 215 that includes a workflow for processing health events, according to one embodiment described herein. As described above, a health event or biometric data received from the sensors is forwarded from the load balancer 205 to the event engine 215. Specifically, a data service node 114A in the workflow receives the forwarded information from the load balancer 205. If the load balancer 205 forwards a health event, the data service node 114A classifies the health event based on type (e.g., a cardiac, respiratory, or maintenance event). In some cases, the health event was classified before being received by the data service node 114A. Nonetheless, the data service node 114A may review the data associated with the health event such as ECG data, breathing rate, blood pressure, etc. using more compute intensive techniques to determine whether the initial classification was correct. In another example, the data service node 114A may provide a more detailed classification of the health event than the initial classification. For example, the sensor device may have generated the health event because it detected an irregular heartbeat. However, the data service node 114A may evaluate the heartbeat and classify the health event as a specific cardiac health event—e.g., a ventricular trigeminy event or an atrioventricular block event. The data service node 114A may save the classification of the health event which is used by downstream nodes and queues to process the health event.

Instead of receiving a health event, the data service node 114A may receive raw data or observations from the patient environment. That is, the raw data or observations may not have been evaluated by a sensor device worn by the patient to determine if this data triggers a health event. For example, observation data from a sensor includes blood pressure measurements, weight measurements, ECG data, and the like. As discussed below, the event engine 215 evaluates these observations and can trigger health events which are then processed in the engine 215.

The data service node 114A forwards the observations to the observation queue 115A and the health events to the events queue 115B. A filter node 114B pulls the observations and health events stored in the queues 115A and 115B. This node 114B serves as a gatekeeper that determines where the health events and observations are routed for further processing. When evaluating observations, the filter node 114B may determine whether to ignore (i.e., drop) the observations or forward the observations to a derived observation queue 115E. For example, observations such as low battery signals, start signals indicating a sensor device has started collecting biometric data, or stop signals indicating a sensor device has stopped may be ignored by the filter service node 114B. In contrast, the node 114B may forward observations such as weight measurements, blood pressure measurements, ECG data, and the like to the derived observation queue 115E. In this manner, the filter service node 114B screens the incoming observations to determine whether they should be processed further such as checking for triggering health events.

Observations forwarded by the filter service node 114B are then processed by a derived observation service node 114C. This node 114C uses received observations in conjunction with previously received observations to create new observations or to generate a new health event. Stated differently, the derived observation service 114C may aggregate previously received observations with the currently received observations to compute statistics, trends, trigger health events, and the like. Although not shown, node 114C may be communicatively coupled to the data repository which stores past observations. For example, if the currently received observation is a weight measurement, the derived observation service node 114C may evaluate this measurement with previous weight measurements to determine a weight change for the patient over a defined period of time. This weight change may trigger a health event which is then forwarded to the data service node 114A for further processing. Even if a health event is not triggered, the derived observation service node 114C may store a derived observation (e.g., a weight change, average blood pressure, heart rate trends, etc.) in the data repository so that this data is available when further observations for the patient are received by the event engine 215 (or other event engines 215).

In one embodiment, health events may be processed by the derived observation service node 114C. For example, a sensor device may trigger a health event upon determining a patient's average blood pressure for a day exceeds a threshold. The filter service node 114B may forward this health event to the derived observation service node 114C which then may use past blood pressure measurements for that patient to derive a weekly or monthly average blood pressure for the patient, or a blood pressure trend graph. Based on this derived observation, the node 114C may generate a new health event or decide to drop the health event if the derived observation does not satisfy a corresponding condition.

Further, filter service node 114B also includes logic for determining whether received health events should be dropped, forwarded to an event action queue 115D, or forwarded to the event rule evaluation queue 115C. For example, a system administrator may determine that some health events are not relevant for certain patients. The logic in the filter service node 114B may identify and drop these health events to prevent them from propagating through the rest of the event engine 215. For instance, a patient may have a heart murmur that constantly results in a sensor device triggering a health event. Rather than continually processing these health events, a care provider can instruct the filter service node 114B to screen out (or suppress) these health events from the patient.

If a received health event has a corresponding action or actions, the filter service nodes 114B forwards the health event to the event action queue 115D. However, if the action for a health event has not yet been identified, the filter service node 114B forwards the health event to the event rule evaluation queue 115C. A rule engine service node 114D pulls the health events from the queue 115C and evaluates the health event using one or more rules. Example rules include determining whether daily weight change and average blood pressure exceed respective thresholds. Based on this evaluation, the node 114D may determine what action the event engine 215 should perform—e.g., suppress/ignore the event, auto handle the event, display the event to a care provider, or delay processing the event. Once the action is determined, the rule engine service node 114D generates and forwards a new health event that includes the corresponding action to the data service node 114A. Now that the corresponding action is known, once the new health event reaches the filter service node 114B, it forwards the event to the event action queue 115D rather than the event rule evaluation queue 115D.

The rule engine service node 114D may delay processing the health event by forwarding the event to a deferred action queue 115F. The node 114D may do so when there is not enough available computing power to perform the rule evaluation or if the rule evaluation has not yet completed. That is, if all of the rules have not yet been evaluated and further evaluation is required before triggering the event action, then the event may be placed in queue 115F. For example, the rule may trigger a cardiac event but the system must first check to determine if that event is suppressed for the patient before taking the corresponding action. As shown, the health events stored in the deferred action queue 115F are then retrieved by the filter service node 114B and can be reintroduced into the event rule valuation queue 115C at a later time—i.e., when all the rules have been evaluated.

Once a corresponding action for a health event is known and the health event is stored in the event action queue 115D, an action engine service node 114E routes the health event to the appropriate action service—i.e., auto handler service 320, notification service 325, or monitoring service 330. The auto handler service 320 may perform actions that do not require supervision or input by a care provider—e.g., stores the health event in the data repository. As another example, the auto handler service 320 may assign a priority or severity to the health event before the event is reintroduced into the workflow with the new priority. The auto handler service 320 may also generate a new health event when, for example, a health event shows a cardiac event but the data quality is low. In response, the service 320 may introduce a maintenance event for checking the sensor connection/electrodes.

The event engine 215 uses notification service 325 to send information to the patient, a care giver, car provider, or device regarding the health event. The notification service 325 may include different communication channels or techniques for communicating with the patient such as email, chat, SMS messages, etc. Although FIG. 3 illustrates only one notification queue 115H and notification engine service node 114G for handling requests, the event engine 215 may have different queues and notification nodes for the different communication techniques. For example, if a maintenance event is triggered when an electrode is unplugged from a sensor device, the notification service 325 may transmit an email to the patient's mobile device instructing the patient to plug in the electrode. Alternatively, if a respiratory event is triggered because of an elevated breathing rate, the notification service may send an SMS message to the patient asking her if she is currently performing a physical activity.

The monitoring service 330 communicatively couples the event engine 215 to the monitoring system 117. When input from a care provider regarding a health event is desired, the monitoring service 330 forwards the health event to a monitoring queue 115G. The UI manager 220 in the monitoring system 117 includes a workflow manager node 305 that pulls health events from the monitoring queue 115G and assigns them to either task queue 310A or 310B. The UI manager 220 also includes task manager nodes 315A and 315B which generate UIs for the health events. These UIs are then displayed to care providers via the computing devices 120A and 120B. Further, the task manager nodes 315 may place the biometric or maintenance data associated with the health events in the UIs. For example, a UI for a cardiac event may display an ECG graph and a baseline chart, while a UI for respiratory event displays a breathing rate and oxygen levels in the blood. In this manner, the UI manager 220 can generate a customized UI for the different health events.

The computing devices 120 may transmit information to the data service node 114A of the event engine 215 which can be used to generate new health events or update current health events. For example, the care provider may instruct the event engine 215 to take a certain action such as forwarding the health event to a different care provider to get a second opinion, reclassifying the health event, suppressing or ignoring the health event, notifying a health care provider, and the like. Based on the care provider's input, the event engine 215 again routes the health event through the nodes 114 and queues 115.

The event engine 215 also includes a task evaluation service node 114F. Unlike the other nodes and queues in event engine 215 which process or store observation data or health events received from the patient environment, the task evaluation service node 114F determines whether to trigger a health event based on a care protocol or care plan. In one embodiment, the node 114F triggers a health event when the patient does not follow the care protocol or plan. For example, the care protocol may ask that the patient wear a sensor device for certain amount of time during the day or take weight measurements each day. By monitoring the observation and health events received by the event engine 215, the task evaluation service node 114F determines whether the patient has complied with the care protocol. If not, the task evaluation service node 114F triggers a health event with a corresponding action for the event engine 215 to perform such as sending a notification to the patient using notification service 325 or informing a care provider using the monitoring service 330.

Machine Learning Architecture

Figure 4:
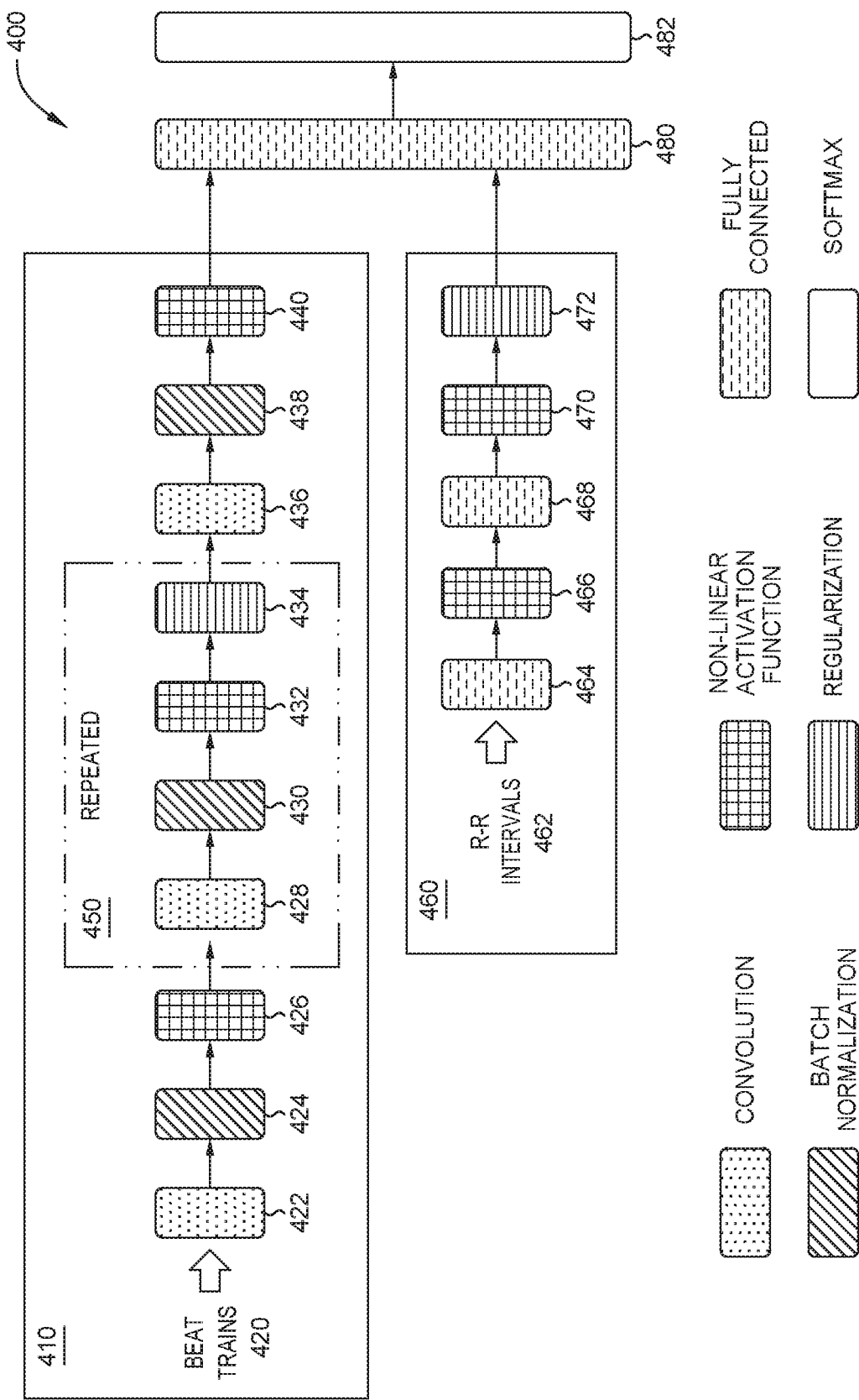
FIG. 4 illustrates a machine learning model, according to one embodiment described herein.

FIG. 4 illustrates a machine learning model 400, according to one embodiment described herein. The machine learning model 400 incorporates two paths. The first path is a deep convolutional neural network 410. The second path is a deep fully-connected neural network 460. The deep convolutional neural network 410 receives one or more beat trains 420. These beat trains 420 can be, for example, ECG waveform data representing groups of three heartbeats assembled from consecutive heartbeats. In an embodiment, the beat trains 420 originate from a half second window of ECG data. In other embodiments, the beat trains 420 could originate from longer, or shorter, windows of ECG data. Three beats is merely an example, and other numbers of beats could be used.

The beat trains 420 are sent through a series of layers in the deep convolutional neural network 410. The beat trains 420 pass through a first collection of layers: a convolution layer 422, a batch normalization layer 424, and a non-linear activation function layer 426. In an embodiment, the convolution layer 422 performs convolution on the time series data in the beat trains 420, the batch normalization layer 424 normalizes the output from the convolution layer 422 (e.g., centering the results around an origin), and the non-linear activation function layer 426 receives the normalized values from the batch normalization layer 424. In an embodiment, the non-linear activation function layer 426 is a Rectified Linear Unit ("ReLU"). Alternatively, other activation functions can be used.

The beat trains then pass through a repeating set of layers 450. The set is made up of: a convolution layer 428, a batch normalization layer 430, a non-linear activation function layer 432, and a regularization layer 434. In an embodiment, the regularization layer 434 performs regularization techniques on the output of the non-linear activation function 432. In an embodiment, the regularization layer 434 is a dropout layer. Alternatively, other regularization layers can be used.

In an embodiment, this set of layers 450 is repeated multiple times. In one example, this set of layers 450 can be repeated ten times. In other examples, the set of layers 450 can be repeated more, or fewer, than 10 times. In an embodiment, different layers in the set of layers 450 can have different hyper parameters (e.g. filter sizes, etc.). Further, in an embodiment, a feed-forward loop, a feed-back loop, or both, can be added to the set of layers 450.

The beat trains 420 then pass through another collection of layers: a convolution layer 436, a batch normalization layer 438, and a non-linear activation function layer 440. As discussed above, in an embodiment, one or more of the non-linear activation function layers 426, 432, and 440, can be a ReLU. Alternatively, other activation functions could be used.

As noted above, the set of layers 450 includes regularization layer 434. In an embodiment, including the regularization layer 434 in the repeated set of layers 450, but not before or after that set of layers 450 (e.g., not in the group of layers 422, 424, 426, and not in the group of layers 436, 438, and 440), can improve the performance of the machine learning model 400. Alternatively, the series of layers 422, 424, 426, or the series of layers 436, 438, 440, can include one or more regularization layers. Further, in an embodiment, the machine learning model 400 includes all of the layers illustrated in FIG. 4. In other embodiments, one or more of these layers can be left out. For example, one or more of the batch normalization layers 424, 430, and 438 can be left out of the deep convolutional neural network 410. One or more of the regularization layers 434 can also be left out.

The deep fully connected neural network 460 receives RR-Interval data 462. This data relates to time intervals between beats, for example for the beats provided in the beat train data 420. In an embodiment, the beat train data 420 provided to the deep convolutional neural network 410 includes waveform information about the beats, but does not include time interval information about the time between beats. This time interval information is provided in the R-R interval data 462, provided to the deep fully connected neural network 460. In an embodiment, four types of R-R interval data can be included in the R-R interval data 462. $RR_{previous}$ relates to the time interval between the subject beat and the previous beat. $RR_{next}$ relates to the time interval between the subject beat and the next beat. $RR_{local\_mean}$ relates to the mean of a number of beats surrounding the subject beat (e.g., a mean of six beats surrounding the subject beat). And $RR_{global\_mean}$ relates to the mean for the entire strip of beats.

According to an embodiment, R-R interval data is provided to the deep fully connected neural network 460. But other types of time interval data could be provided instead. Further, other types of data other than time interval data could be provided. For example, patient demographic data (e.g., gender, age, weight, activity level, etc.) could be included. Further, environmental data (e.g., the time the data was collected) could be included.

The deep fully connected neural network 460 includes a series of layers: a fully connected layer 464, a non-linear activation function layer 466, another fully connected layer 468, another non-linear activation function layer 470, and a regularization layer 472 (e.g., a dropout layer, as discussed above with regard to the regularization layer 434). In an embodiment, one or more of the non-linear activation function layers 466 and 470 can be a ReLU. Further, in an embodiment, the deep fully connected neural network 460 includes all of the layers illustrated in FIG. 4. In other embodiments, one or more of these layers can be left out. For example, the regularization layer 472 can be left out.

The output from the two paths is then provided to the fully connected layer 480. In an embodiment, the output from the deep convolutional neural network 410 is flattened, and concatenated with the output of the deep fully connected neural network 460. The resulting values are passed through a fully connected layer 480 and a softmax layer 482. This produces probability distributions for the beat classes. As discussed above, in one embodiment, this combination of the output from the deep convolutional neural network 410 (e.g., the output from the non-linear activation layer 440) with the output from the neural network 460 (e.g., the output from the regularization layer 472) provides improved performance for the machine learning model 400. For example, analyzing unstructured heartbeat data using the deep convolutional neural network 410 while analyzing structured R-R interval data using the fully connected neural network 462 can improve performance of the model, including accuracy. In an embodiment, the fully connected layer 480 can be a single fully connected layer. Alternatively, the fully connected layer 480 can be made up of multiple layers, including multiple fully connected layers and multiple additional layers (e.g., similar to the neural network 460).

In an embodiment, the neural network 460 operates on structured data, while the deep convolutional neural network 410 operates on unstructured data. In an embodiment, additional, or different, unstructured data can be analyzed using the deep convolutional neural network 410. For example, medical imaging data, medical time series data, or other data could be used. In an embodiment, each type of unstructured data provided to the deep convolutional neural network 410 traverses its own path, while the structured data provided to the neural network 460 all traverses the same path.

Figure 5:
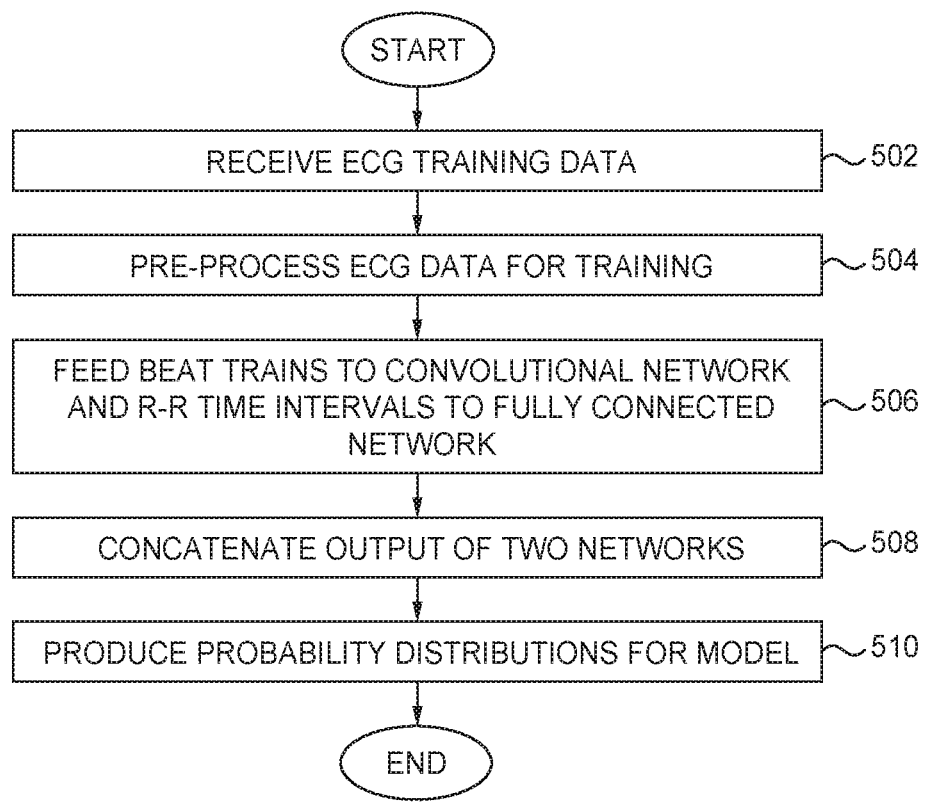
FIG. 5 is a flow chart illustrating training a machine learning model for classifying heartbeat data, according to one embodiment described herein.

FIG. 5 is a flow chart illustrating training a machine learning model (e.g., the machine learning model 400 illustrated in FIG. 4) for classifying heartbeat data, according to one embodiment described herein. As used herein, "trained machine learning" is used interchangeably with "supervised machine learning," and generally refers to machine learning that utilizes exemplars and pre-determined attribute scores to train the model. At block 502, ECG training data is received. This data can be generated by, for example, a wearable MCT device. At block 504, the ECG training data is pre-processed. For example, feature vectors can be generated using the ECG training data. These feature vectors can be used to train the deep learning model. In an embodiment, two categories of information are generated: time interval information related to RR-intervals between heartbeats and waveform beat train information. In an embodiment, the beat train can include raw ECG waveform data. Further, in an embodiment, the ECG data can be pre-labeled with classifications of beats to facilitate training of the deep learning model. In an embodiment, the machine learning model 400 can be trained without requiring time consuming patient-specific labeling of training data.

At block 506, this information is fed into a two-path deep learning model for training. In an embodiment, the RR-interval information is fed into a deep fully connected neural network. In an embodiment, this can be the deep fully connected neural network 460 illustrated in FIG. 4. Beat train waveform data is fed into a deep convolutional network. In an embodiment, this can be the deep convolutional neural network 410 illustrated in FIG. 4. At block 508, the two paths of the deep learning model are joined (e.g., using the fully connected layer 480 illustrated in FIG. 4). The output of the fully connected neural network is concatenated with the flattened output of the deep convolutional network. At block 510, probability distributions for the relevant beat classes are generated based on the concatenated outputs from block 508.

In embodiment, the deep learning model, for example the machine learning model 400 illustrated in FIG. 4, can classify cardiac irregularities. For example, the machine learning model 400 can classify each heartbeat as one of three states: VEB, NOT_VEB, and NOT_A_BEAT. In one embodiment, the deep learning model (e.g., the machine learning model 400) can be used to verify previously detected beats. Beats can be detected in the ECG data using known fully-automated beat detection algorithms. These algorithms can be highly accurate (>99%), but they are not perfect. The deep learning model can determine whether a portion of ECG data initially identified as a beat is actually a beat, and can fix any false positives. Alternatively, in another embodiment, the deep learning model can be used to initially detect beats in the ECG data.

Further, while embodiments herein are discussed in relation to classifying VEBs, the disclosed techniques could be used to classify any number of cardiac events and irregularities. For example, the disclosed techniques could be used to classify supra-ventricular ectopic beats. In this example, the output of the machine learning model 400 could be NORMAL, VEB, SUPRA-VEB, NORMAL-VEB_FUSION, and QUESTIONABLE. The disclosed techniques could further be used to identify sub-classifications of these labels (e.g., sub-classifications of VEB or SUPRA-VEB). For example, the configuration of the final fully connected layer (e.g., the fully connected layer 480 illustrated in FIG. 4) could be changed to output more, or fewer, classifications. Further, the disclosed embodiments could be used to classify other types of data.

Figure 6:
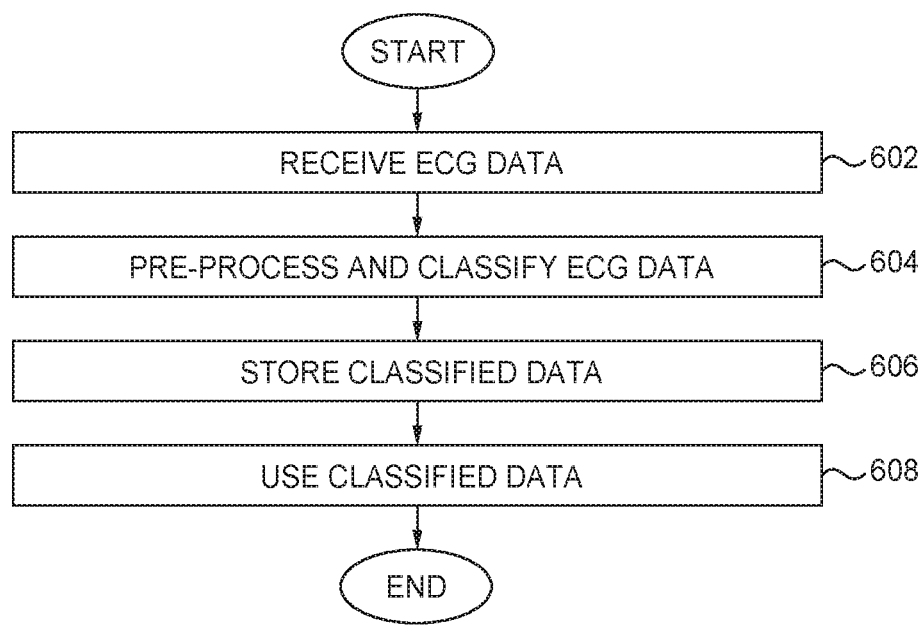
FIG. 6 is a flow chart illustrating using a machine learning model, to classify heartbeats for a patient, according to one embodiment described herein.

FIG. 6 is a flow chart illustrating using a machine learning model (e.g., the machine learning model 400), to classify heartbeats for a patient, according to one embodiment described herein. At block 602, the machine learning model 400 receives ECG for a patient. This data can be generated by, for example, a wearable MCT device. In an embodiment, this data can be newly received ECG data. In another embodiment, this data can be previously classified ECG data. The machine learning model can be used to re-classify, or verify, previously classified ECG data.

At block 604, the data is pre-processed (as appropriate) and the machine learning model classifies the ECG data. For example, the ECG data can be pre-processed to identify waveform ECG data and time interval data. The resulting data is fed into the machine learning model, and is classified by the machine learning model. In an embodiment, known beat detection algorithms can be used to identify beats in the ECG data. This can be used to generate waveform data and time interval data relating to the beats in the ECG data. Alternatively, the machine learning model 400 can be used to detect beats as well as classify detected beats. In an embodiment, waveform data is provided to a path comprising a convolutional neural network (e.g., the convolutional neural network 410 illustrated in FIG. 4) while time interval data is provided to a path comprising a fully connected neural network (e.g., the neural network 460 illustrated in FIG. 4). The output from these paths is concatenated (e.g., using the fully connected layer 480 illustrated in FIG. 4).

In an embodiment, the machine learning model can classify the beats reflected in the ECG data. For example, as discussed above, the machine learning model can classify cardiac irregularities. In another embodiment, the machine learning model can generate a confidence interval or probability for the classification of each beat. At block 606, the classified data is stored in a data repository, for example data repository 118 illustrated in FIGS. 1 and 2.

At block 608, the classified data is used to inform and treat the patient. For example, the machine learning model can identify cardiac irregularities (e.g., VEB) by classifying heartbeats. Devices in the computing environment (e.g., the computing environment 100 illustrated in FIG. 1) can then be used to treat the cardiac irregularity in the patient. For example, a particular treatment (e.g., a medication or a patient behavior) for the cardiac irregularity identified using the machine learning model could be recommended to the patient using the patient's mobile device (e.g., the mobile device 135 illustrated in FIG. 1). As another example, a report could be generated for a physician treating the patient, using the classified data. Alternatively, a report could be generated for the patient him or herself. Further, a patient care plan could be generated or modified based on the classified. For example, a patient care plan for a patient could be generated based on the classification. The patient care plan could provide treatment options (e.g., medication, educational content, behavioral changes, etc.) for the patient based on the classification. Further, an existing care plan for the patient could be modified.

In addition, an alert or output could be generated for the patient, care provider, or other interested parties. For example, an alert could be provided to the patient using a graphical user interface on a device operated by the patient (e.g., a mobile device 135 as illustrated in FIG. 1 or computer). Alternatively, an alert could be provided to the patient's care provider using a graphical user interface on a device operated by the care provider (e.g., a mobile device or a computing device 120 as illustrated in FIG. 1).

The deep learning model can operate in a variety of locations. For example, the deep learning model can operate as part of the care provider environment 105 (e.g., on workflow server 110, computing device 120, or monitoring system 117). The model can operate on a physical computing system or a virtual computer instance (e.g., a cloud computing platform). Further, the deep learning model can operate on a device in the patient environment 130, including mobile device 135 and sensor devices 140. The deep learning model can be computationally intensive, however, and so the mobile device 135 or sensor devices 140 (or any of the devices in care provider environment 105) can include specialized hardware for training and running the deep learning model.

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational blocks to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

I claim:

1. A computer-implemented method for classifying heartbeats using patient electrocardiogram (ECG) data, comprising:
   receiving the ECG data, the ECG data comprising unstructured waveform data and corresponding structured time interval data relating to a plurality of heartbeats, wherein a mobile device is configured to receive the ECG data from a remote sensor device;
   providing the unstructured waveform data to a convolutional neural network in a first path of a machine learning architecture;
   generating a first plurality of output values by analyzing the unstructured waveform data, without the corresponding structured time interval data, using the convolutional neural network in the first path of the machine learning architecture;
   providing the structured time interval data to a fully-connected neural network in a second path of the machine learning architecture;
   generating a second plurality of output values by analyzing the structured time interval data, without the corresponding unstructured waveform data, using the fully-connected neural network in the second path of the machine learning architecture; and
   classifying one or more of the plurality of heartbeats in the ECG data by concatenating the first plurality of output values generated by the convolutional neural network using the waveform in data and the second plurality of output values generated by the fully connected neural network using the corresponding time interval data, wherein the convolutional neural network comprises a different structure from the fully connected neural network.

2. The computer-implemented method of claim 1, wherein the first plurality of output values and the second plurality of output values are concatenated using a fully connected layer in the machine learning architecture.

3. The computer-implemented method of claim 1, wherein the convolutional neural network comprises a set of connected layers comprising:
   a convolution layer;
   a batch normalization layer;
   an activation function layer; and
   a regularization layer.

4. The computer implemented method of claim 3, wherein the set of connected layers is repeated in the convolutional neural network.

5. The computer implemented method of claim 4, wherein the set of connected layers is repeated at least ten times in the convolutional neural network.

6. The computer implemented method of claim 4, wherein the convolutional neural network further comprises a plurality of convolution layers, a plurality of batch normalization layers, and a plurality of activation function layers, in addition to the set of connected layers.

7. The computer-implemented method of claim 1, wherein the second path does not comprise a convolution layer and wherein the second path comprises a deep fully-connected neural network.

8. The computer-implemented method of claim 1, wherein classifying one or more of the plurality of heartbeats in the ECG data comprises: verifying, using the machine learning architecture, that the heartbeat comprises a beat, based on the concatenated first plurality of output values and second plurality of output values.

9. The computer-implemented method of claim 1, further comprising:
   processing the ECG data to generate the waveform data and the time interval data, the processing comprising identifying the plurality of heartbeats in the ECG data.

10. The computer-implemented method of claim 1, wherein classifying one or more of the plurality of heartbeats in the ECG data comprises classifying the one or more heartbeats as Ventricular Ectopic Beats (VEBs).

11. A computer program product for classifying heartbeats using patient electrocardiogram (ECG) data, the computer program product comprising:
a computer-readable storage medium having computer-readable program code embodied therewith, the computer-readable program code executable by one or more computer processors to perform an operation, the operation comprising:
receiving the ECG data, the ECG data comprising unstructured waveform data and corresponding structured time interval data relating to a plurality of heartbeats;
providing the unstructured waveform data to a convolutional neural network in a first path of a machine learning architecture based on the convolutional neural network being configured to analyze unstructured data;
generating a first plurality of output values by analyzing the unstructured waveform data, without the corresponding structured time interval data, using the convolutional neural network in the first path of the machine learning architecture;
providing the structured time interval data to a fully-connected neural network in a second path of the machine learning architecture based on the fully-connected neural network being configured to analyze structured data;
generating a second plurality of output values by analyzing the structured time interval data, without the corresponding unstructured waveform data, using the fully-connected neural network in the second path of the machine learning architecture; and
classifying a heartbeat of the plurality of heartbeats in the ECG data by concatenating the first plurality of output values generated by the convolutional neural network using the waveform data and the second plurality of output values generated by the fully-connected neural network using the corresponding time interval data, using the machine learning architecture, wherein the convolutional neural network comprises a different structure from the fully connected neural, network, comprising:
verifying, using the machine learning architecture, that the heartbeat comprises a beat, based on the concatenated first plurality of output values and second plurality of output values; and
determining, based on the concatenated first plurality of output values and second plurality of output values, a probability that the heartbeat comprises a ventricular ectopic beat (VEB).

12. The computer program product of claim 11, wherein the first plurality of output values and the second plurality of output values are concatenated using a fully connected layer in the machine learning architecture.

13. The computer program product of claim 11, wherein the convolutional neural network comprises a set of connected layers comprising:
a convolution layer;
a batch normalization layer;
an activation function layer; and
a regularization layer, and
wherein the set of connected layers is repeated in the convolutional neural network.

14. The computer program product of claim 11, wherein classifying one or more of the plurality of heartbeats in the ECG data comprises identifying a cardiac irregularity based on the ECG data, the operation further comprising:
providing treatment to a patient for the cardiac irregularity based on the classified one or more heartbeats.

15. A system, comprising:
a processor; and
a memory storing a program, which, when executed on the processor, performs an operation, the operation comprising:
receiving patient electrocardiogram (ECG) data;
pre-processing the ECG data, comprising:
detecting a plurality of heartbeats based on the ECG data;
generating unstructured waveform data relating to the detected plurality of heartbeats; and
generating corresponding structured time interval data relating to the plurality of heartbeats;
providing the unstructured waveform data to a convolutional neural network in a first path of a machine learning architecture based on the convolutional neural network being configured to analyze unstructured data;
generating a first plurality of output values by analyzing the unstructured waveform data, without the corresponding structured time interval data, using the convolutional neural network in the first path of the machine learning architecture;
providing the structured time interval data to a fully-connected neural network in a second path of the machine learning architecture based on the fully-connected neural network being configured to analyze structured data;
generating a second plurality of output values by analyzing the structured time interval data, without the corresponding unstructured waveform data, using the fully-connected neural network in the second path of the machine learning architecture; and
classifying a heartbeat of the plurality of heartbeats in the ECG data by concatenating the first plurality of output values generated by the convolutional neural network using the waveform data and the second plurality of output values generated by the fully-connected neural network using the corresponding time interval data, wherein the convolutional neural network comprises a different structure from the fully connected neural network.

16. The system of claim 15, wherein the first plurality of output values and the second plurality of output values are concatenated using a fully connected layer in the machine learning architecture.

17. The system of claim 15, wherein the convolutional neural network comprises a set of connected layers comprising:
a convolution layer;
a batch normalization layer;
an activation function layer; and
a regularization layer, and
wherein the set of connected layers is repeated in the convolutional neural network.

18. The system of claim 17, wherein the set of connected layers is repeated at least ten times in the convolutional neural network.

19. The system of claim 15, wherein classifying one or more of the plurality of heartbeats in the ECG data comprises verifying, using the machine learning architecture, that the heartbeat comprises a beat, based on the concatenated first plurality of output values and second plurality of output values.

20. The system of claim 15, wherein classifying one or more of the plurality of heartbeats in the ECG data comprises classifying the one or more heartbeats as Ventricular Ectopic Beats (VEBs).

* * * * *